United States Patent [19]
Gander et al.

[11] Patent Number: 4,969,578
[45] Date of Patent: Nov. 13, 1990

[54] DISPENSING APPARATUS
[75] Inventors: Terence W. Gander, Bracknell; Jeremy K. McCullagh, Reepham, both of United Kingdom
[73] Assignee: Bespak PLC, Norfolk, United Kingdom
[21] Appl. No.: 348,361
[22] Filed: May 8, 1989
[51] Int. Cl.⁵ ............................................. B65D 83/14
[52] U.S. Cl. ................................ 222/131; 128/200.23; 222/162; 222/182; 222/183
[58] Field of Search ................. 222/94, 105, 131, 162, 222/175, 182, 183, 325, 402.11, 402.13; 128/203.23, 203.28, 200.23

[56] References Cited
U.S. PATENT DOCUMENTS
3,195,777 7/1965 Hart ..................................... 222/182
3,622,053 11/1971 Ryden ............................ 222/402.11

FOREIGN PATENT DOCUMENTS
1061296 8/1979 Canada ................................ 222/215

Primary Examiner—Andres Kashnikow
Attorney, Agent, or Firm—Beveridge, DeGrandi & Weilacher

[57] ABSTRACT

A dispensing apparatus for nasal administration of an aerosol product is provided with a housing for a pressurized dispensing container with a pivoted cover which in its closed position encloses an outlet duct of the housing. The container is received in a chamber of the housing which is sealed by a bellows portion. An openable closure provides access to the chamber for insertion and removal of the container. The apparatus seals the chamber against ingress of foreign matter between use and encloses the outlet duct to prevent soiling.

6 Claims, 2 Drawing Sheets

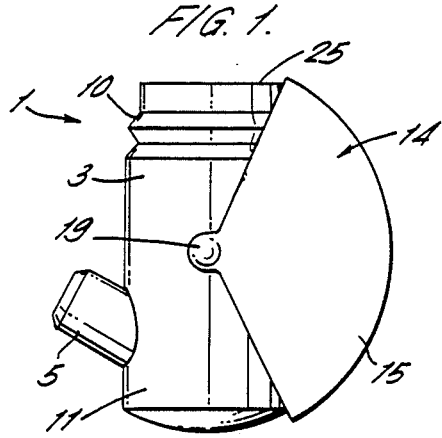
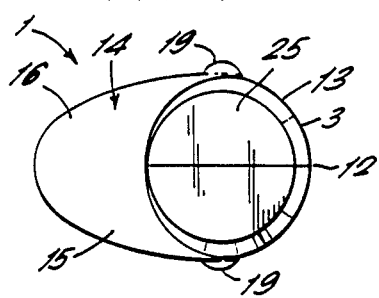
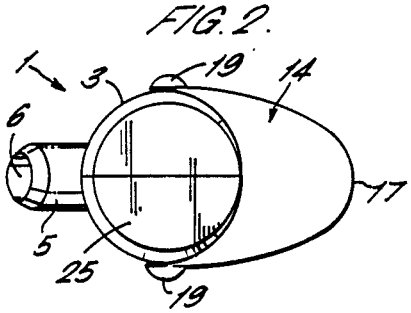
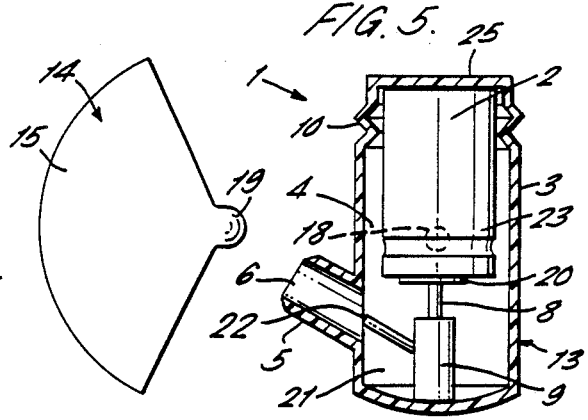
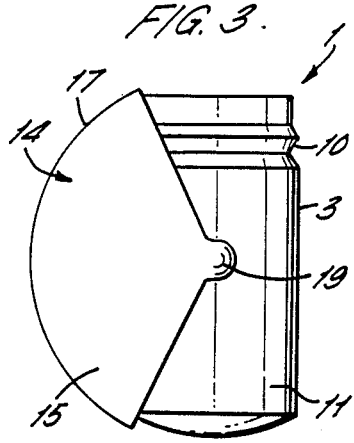
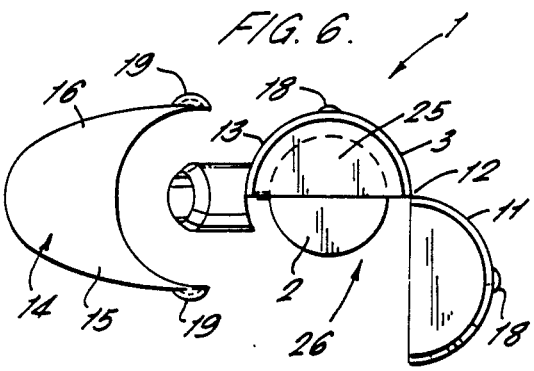

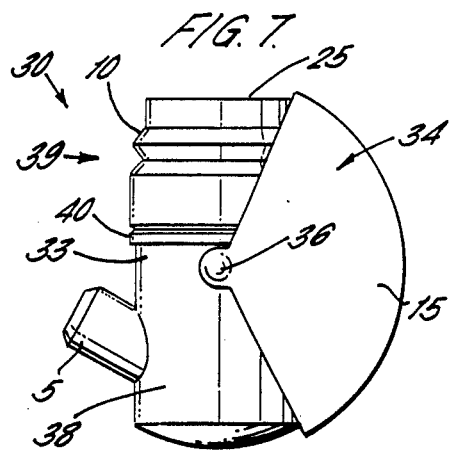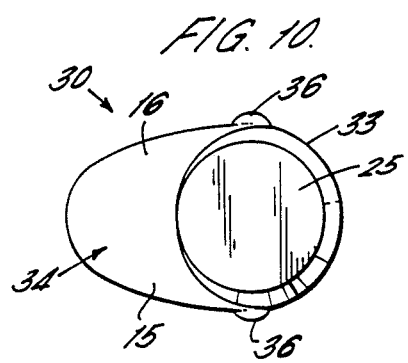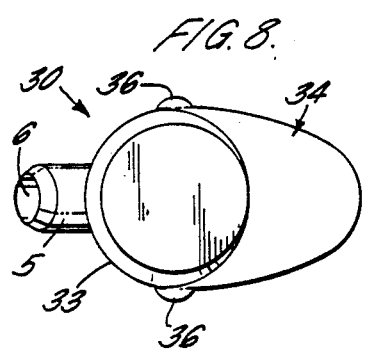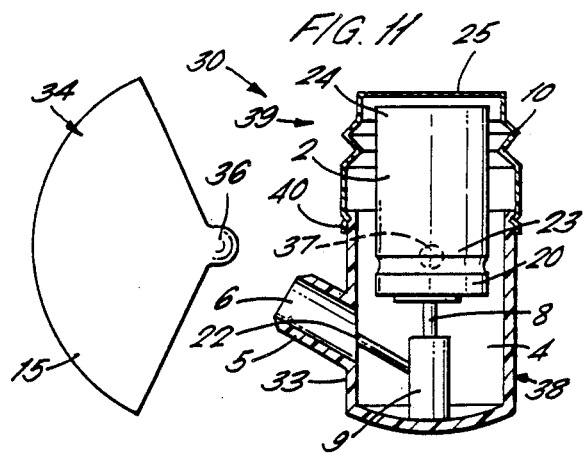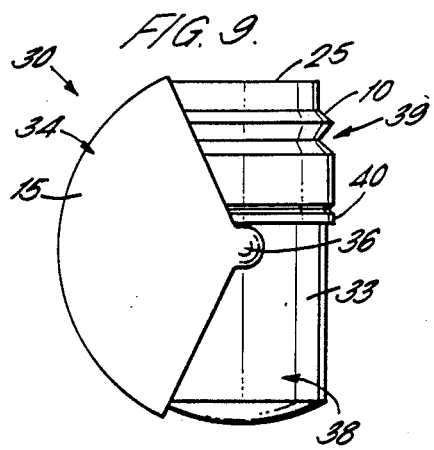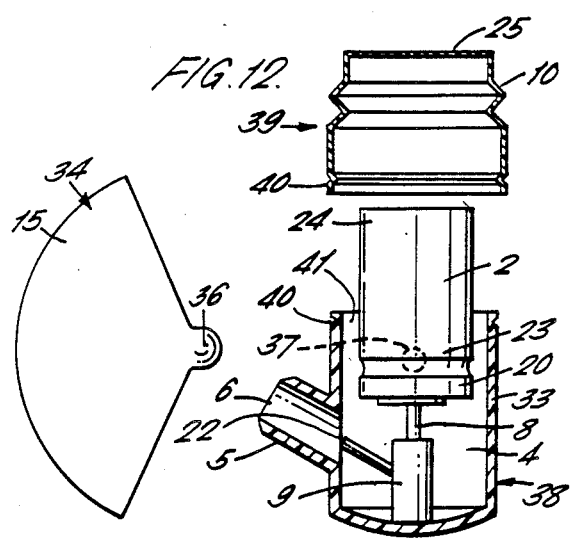

DISPENSING APPARATUS

This invention relates to dispensing apparatus for use with a pressurised dispensing container and in particular but not exclusively to dispensing apparatus for nasally administering medicinal products in aerosol form.

It is known to provide dispensing apparatus comprising a housing defining a chamber for a pressurised dispensing container and an outlet duct through which a product may be dispensed in aerosol form. The housing generally provides for axial movement of a cylindrical container such that a valve of the container is actuated in response to relative movement between the container and the housing.

A problem associated with such apparatus is that the outlet duct is susceptible to contamination by the ingress of foreign matter when the apparatus is not in use and the external surfaces of the outlet duct may become soiled. A further problem is that the housing must include an access aperture through which access may be gained to the pressurised dispensing container in order to insert a fresh container or remove the container to permit cleansing of the housing, this aperture also providing a point of entry for contamination to the chamber.

It is known from EP-0075548 to provide a cover which is pivotally connected to the housing and movable such that in a closed position the cover encloses both the access aperture and the outlet duct and in an open position both the aperture and outlet duct are exposed. In the open position the container is accessible through the access aperture so that a user can manually depress the container such that a dispensing valve of the container is actuated by engagement with a valve actuator having a nozzle formed in the housing adjacent to the outlet duct.

It has been found that even with such a cover contamination of the chamber with foreign matter such as dust continues to be a problem because the access aperture opens whenever the outlet duct is uncovered for use.

It has also been proposed in US-3,429,310 to provide an access aperture which is normally closed by a closure in the form of a cap which is slidably mounted on the main body of the housing so that movement of the cap causes actuating movement of the container. In this arrangement however although the outlet of the outlet duct is covered between use by a flap the external surfaces of the outlet duct are always exposed and liable to become soiled.

According to the present invention a dispensing apparatus for a pressurised dispensing container containing a product to be dispensed, the apparatus comprising a housing defining a chamber within which the container is slidably received in use, an outlet duct communicating with the chamber for the discharge of dispensed product in aerosol form, a cover hingedly connected to the housing and movable between a closed position in which the outlet duct is enclosed and an open position in which the outlet duct is exposed for use, the housing comprising a valve actuator connected to a nozzle adjacent the outlet duct and cooperating with a dispensing valve of the container in use to dispense an aerosol spray through the outlet duct, the valve being actuated by displacement of the container towards the valve actuator, the housing defining an access aperture through which the container may be inserted or removed, wherein the housing includes an openable closure normally sealing the access aperture and the housing further comprises a bellows portion defining an end wall of the chamber which is movable relative to the actuator to provide an actuating stroke of the container.

An advantage of such an arrangement is that the access aperture is only opened during insertion or removal of a container so that the chamber is normally sealed apart from the presence of the outlet duct so that the ingress of foreign matter is minimised. Furthermore the external surfaces of the outlet duct are enclosed when the apparatus is not in use thereby preventing soiling.

The closure may comprise a side portion hingedly connected to a main body of the housing and may conveniently be hingedly connected by means of a membrane hinge.

Alternatively the closure may be an end cap including the bellows portion and may be formed of a plastics material of greater flexibility than that of the main body. The end cap may conveniently be a snap fit with the main body of the housing.

Embodiments of the present invention will now be described by way of example only and with reference to the accompanying drawings of which:

FIG. 1 is a side elevation of a first embodiment showing a dispensing apparatus with the cover in the open position;

FIG. 2 is a plan view of the apparatus of FIG. 1 with the cover in the open position;

FIG. 3 is a side elevation of the apparatus in FIGS. 1 and 2 with the cover shown in the closed position;

FIG. 4 is a plan view of the apparatus of FIG. 3 with the cover in the closed position;

FIG. 5 is a partly sectioned exploded view of the apparatus of FIGS. 1 to 4;

FIG. 6 is an exploded plan view of the apparatus of FIGS. 1 to 5 showing the access aperture in an open condition;

FIG. 7 is a side elevation of a second embodiment showing a dispensing apparatus with the cover in the open position;

FIG. 8 is a plan view of the apparatus of FIG. 7 with the cover in the open position;

FIG. 9 is a side elevation of the apparatus of FIGS. 7 and 8 with the cover in the closed position;

FIG. 10 is a plan view of the apparatus of FIGS. 7 to 9 with the cover in the closed position;

FIG. 11 is a sectional elevation of the apparatus of FIGS. 7 to 10; and

FIG. 12 is an exploded elevation of the apparatus of FIGS. 7 to 11 showing the access aperture in an open condition.

The first embodiment of the invention as shown in FIGS. 1 to 6 comprises a dispensing apparatus 1 containing a cylindrical pressurised dispensing container 2. The apparatus 1 has a housing 3 of polypropylene defining a cylindrical chamber 4 within which the container is located. An outlet duct 5 projects from the housing 3 and communicates between a lower end 21 of the chamber 4 and an outlet 6. The container 2 has a dispensing valve 20 having valve actuating stem 8 which is received in a valve actuator 9 which forms part of the housing 3 and is located at the lower end 21 of the chamber 4. The valve actuator 9 is arranged such that product dispensed through the stem 8 is directed by the actuator through a nozzle 22 in a direction such that an aerosol mist is discharged through the duct 5 and emerges from the outlet 6.

The valve actuating stem 8 extends axially from the lower end 23 of the container 2 and the upper end 24 of the container rests in contact with an end wall 25 of the housing 3. The housing 3 includes a bellows portion 10 adjacent the end wall 25 arranged such that by flexure of the bellows portion the end wall 25 is movable towards and away from the actuator 9.

The housing 3 has a side portion 11 which is hingedly connected by means of a membrane hinge 12 to the main body 13 of the housing, the side portion thereby forming an openable closure to provide an access aperture 26 for loading the container 2 into the chamber 4. The side portion 11 is normally retained in a closed position by snap fit connectors (not shown) operable between the side portion and the main body 13.

A cover 14 comprises a part annular profile of generally U-shaped cross-section and comprising side walls 15 and 16 connected by a part cylindrical connecting wall 17. The side walls 15 and 16 each include hinge formations 19 cooperable with hinge formations 18 on the outer walls of the housing 3, the arrangement being such that the cover 14 is movable between an open position as shown in FIG. 1 in which the cover is disposed on the opposite side of the housing 3 from the duct 5 and a closed position as shown in FIG. 3 in which the cover encloses the duct 5.

In use the apparatus 1 is normally stored in the closed condition as shown in FIGS. 3 and 4 in which the cover 14 shields the outlet duct 5 against the ingress of foreign matter such as dust and prevents soiling of the external surfaces of the duct. When it is required to use the apparatus 1 for dispensing the product the cover 14 is moved into its open position as shown in FIGS. 1 and 2 thereby revealing the outlet duct 5. In this position the cover 14 also does not obstruct access to the bellows portion 10 so that the user holds the housing 3 in one hand with an index finger placed upon the end wall 25. The outlet duct 5 is then nasally inserted and the end wall 25 depressed to move the container 2 towards the actuator 9 with respect to which the stem 8 remains fixed. The valve 20 is then actuated and a quantity of the product is dispensed through the outlet 6 via the nozzle 22. Manual pressure is then released and the container 2 returns to its rest position by virtue of spring action provided by the valve 20 biassing the stem into an extended position.

The container 2 is accessible by means of the openable closure 11 when for example it is necessary to remove the container 2 from the housing 3 to wash the housing after a period of use or when it is required to fit a fresh container. Prior to opening the closure 11 it is necessary to detach the cover 14, this being accommodated by flexure of the side walls 15 and 16. In the closed position of the side portion 11 the chamber 4 is sealed except for the outlet 6.

The apparatus 1 may also be provided with snap fit formations (not shown) for retaining the cover 14 in its open and closed positons respectively.

A second embodiment of the invention is shown in FIGS. 7 to 12 in which corresponding reference numerals have been used where appropriate to those appearing in FIGS. 1 to 6.

Dispensing apparatus 30 as shown in FIGS. 7 to 12 comprises a modified housing 33 having an outlet duct 5 providing communication between a chamber 4 and an outlet 6. A pressurised dispensing container 2 received within the chamber 4 is arranged such that a valve actuating stem 8 is cooperable with an actuator 9 of the dispensing apparatus 30, the container 2 being axially slidably received within the housing 33 such that upon depression of the container an aerosol mist of product is dispensed through the duct 5 from the outlet 6.

The housing 33 is provided with a cover 34 in the form of an oblate hemi-spheroidal shell in which hinge formations 36 are formed at the opposite flattened poles thereof.

The housing 33 is provided with cooperating hinge formations 37, the arrangement being such that the cover 34 is pivotal between an open position as shown in FIGS. 7 and 8 in which the outlet duct 5 is uncovered and a closed position as shown in FIGS. 9 and 10 in which both the duct 5 is enclosed.

As shown in FIGS. 11 and 12 the housing is of two part construction having a main body 38 formed of a rigid plastics material and an end cap 39 formed of a more flexible plastics material. The cap 39 incorporates a bellows portion 10 adjacent an end wall 25 which is movable by bellows action towards and away from the actuator 9.

In FIG. 11 the cap 39 is shown in its normal position in which it forms a seal to the upper end 23 of the chamber 4. The cap 39 is connected to the main body 38 by means of a snap fit connector 40 which is arranged to provide an airtight seal.

As shown in FIG. 12 the cap 39 is separable from the main body 38 to provide an access aperture 41 through which the container may be inserted or removed as required. By suitably positioning the cover 34 relative to the housing 33 it is not necessary to disconnect the cover 34 from the housing prior to removal of the cap 39.

The dispensing operation of the apparatus 30 in use is similar to that described above with reference to dispensing apparatus 1 in that flexure of the bellows portion 10 permits manual depression of the container 2 by finger pressure applied externally to the end wall 25 of the housing 33.

In each case after actuation finger pressure is released and the container returns to its normal rest position under spring action provided by the valve 20 which is arranged to bias the stem 8 into an extended position.

The cover 34 fits snugly to the housing 33 in the closed position so that the apparatus 30 is effectively sealed against the ingress of foreign matter such as dust.

Snap fit formations (not shown) may also be provided for retaining the cover 24 in its open and closed positions respectively.

The construction of the bellows portion 10 may alternatively be such that the container 2 is lightly biassed by resilience of the bellows portion into seating contact with the actuator 9. This bias must however be arranged to be insufficient to actuate the valve 20.

Alternative embodiments of the present invention are possible in which alternative forms of hinge formation are employed, for example by interchanging the male and female hinge components formed on the housing and cover respectively.

The housing and cover are in each case preferably moulded from plastics materials and the cover may be formed from transparent or semi-transparent plastics material.

The outlet duct 5 may alternatively be of a suitable shape for oral insertion.

Where the housing is of two part construction as shown for example in FIGS. 7 to 12 the cap may be formed of the same material as the main body of the housing provided suitable thinning in the region of the bellows portion ensures sufficient flexibility to allow bellows action.

The cap may alternatively be formed of a more flexible plastics material or an elastomeric material such as synthetic rubber.

Where the housing is of one part construction then local thinning in the region of the bellows portion may be necessary to provide sufficient flexibility for bellows action.

I claim:

1. Dispensing apparatus for a pressurised dispensing container containing a product to be dispensed, the apparatus comprising a housing having a body portion defining a chamber within which the container is slidably received in use, an outlet duct formed unitarily with the body portion and projecting at a fixed angle therefrom, the outlet duct communicating with the chamber for the discharge of dispensed product in aerosol form, the outlet duct having a nasally insertable cylindrical external surface, a cover hingedly connected to the housing and movable between a closed position in which the outlet duct is enclosed thereby preventing contamination of the external surface of the outlet duct and an open position in which the outlet duct is exposed for use, the housing comprising a valve actuator connected to a nozzle adjacent the outlet duct and cooperating with a dispensing valve of the container in use to dispense an aerosol spray through the outlet duct, the valve being actuated by displacement of the container towards the valve actuator, the housing defining an access aperture through which the container may be inserted or removed, wherein the housing includes an openable closure normally sealing the access aperture and the housing further comprises a bellows portion defining an end wall of the chamber which is movable relative to the actuator to provide an actuating stroke of the container.

2. Apparatus as claimed in claim 1 wherein the closure comprises a side portion hingedly connected to a main body of the housing.

3. Apparatus as claimed in claim 2 wherein the side portion is connected to the main body by means of a membrane hinge.

4. Apparatus as claimed in claim 1 wherein the closure comprises an end cap including the bellows portion.

5. Apparatus as claimed in claim 4 wherein the end cap is formed of a material of greater flexibility than that of the main body of the housing.

6. Apparatus as claimed in claim 4 wherein the end cap is received as a snap fit on a main body of the housing.

* * * * *